(12) United States Patent
Leobandung (10) Patent No.: US 10,090,429 B2
(45) Date of Patent: Oct. 2, 2018

(54) INTEGRATED ON CHIP DETECTOR AND ZERO WAVEGUIDE MODULE STRUCTURE FOR USE IN DNA SEQUENCING

(71) Applicant: International Business Machines Corporation, Armonk, NY (US)

(72) Inventor: Effendi Leobandung, Stormville, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/605,685

(22) Filed: May 25, 2017

(65) Prior Publication Data

US 2017/0263801 A1  Sep. 14, 2017

Related U.S. Application Data

(62) Division of application No. 14/596,823, filed on Jan. 14, 2015, now Pat. No. 9,666,748.

(51) Int. Cl.
  *H01L 31/18* (2006.01)
  *H01L 31/105* (2006.01)
  (Continued)

(52) U.S. Cl.
  CPC ............ *H01L 31/18* (2013.01); *C12Q 1/6874* (2013.01); *H01L 31/035227* (2013.01); *H01L 31/105* (2013.01)

(58) Field of Classification Search
  None
  See application file for complete search history.

(56) References Cited

U.S. PATENT DOCUMENTS 7,157,053 B2  1/2007  Hahn et al.
8,399,339 B2  3/2013  Lieber et al.
(Continued)

FOREIGN PATENT DOCUMENTS

CN  103824813 A  5/2014
JP  200839655  2/2008
JP  2010172290  8/2010

OTHER PUBLICATIONS

Park, H., et al., "Filter-Free Image Sensor Pixels Comprising Silicon Nanowires with Selective Color Absorption", Nano Lett., Mar. 3, 2014, 14, pp. 1804-1809.
(Continued)

*Primary Examiner* — Robert Carpenter
(74) *Attorney, Agent, or Firm* — Scully, Scott, Murphy & Presser, P.C.; Louis J. Percello, Esq.

(57) ABSTRACT

A semiconductor structure for use in single molecule real time DNA sequencing technology is provided. The structure includes a semiconductor substrate including a first region and an adjoining second region. A photodetector is present in the first region and a plurality of semiconductor devices is present in the second region. A contact wire is located on a surface of a dielectric material that surrounds the photodetector and contacts a topmost surface of the photodetector and a portion of one of the semiconductor devices. An interconnect structure is located above the first region and the second region, and a metal layer is located atop the interconnect structure. The metal layer has a zero waveguide module located above the first region of the semiconductor substrate. A DNA polymerase can be present at the bottom of the zero waveguide module.

18 Claims, 6 Drawing Sheets

(51) Int. Cl.
*H01L 31/0352* (2006.01)
*C12Q 1/68* (2018.01)
*C12Q 1/6874* (2018.01)

(56) References Cited

U.S. PATENT DOCUMENTS

| | | |
|---|---|---|
| 8,575,663 B2 | 11/2013 | Lieber et al. |
| 8,729,502 B1 | 5/2014 | Klotzkin |
| 9,666,748 B2 * | 5/2017 | Leobandung ........... H01L 31/18 |
| 2002/0115293 A1 | 8/2002 | Ghodsian |
| 2011/0024088 A1 | 2/2011 | Lin et al. |
| 2011/0133061 A1 | 6/2011 | Yu et al. |
| 2011/0220943 A1 | 9/2011 | Benaron et al. |
| 2013/0143206 A1 | 6/2013 | McCaffrey et al. |

OTHER PUBLICATIONS

"Pacific Biosciences Develops Transformative DNA Sequencing Technology", Pacific Biosciences Technology Backgrounder, Nov. 24, 2008, 14 pages.
Eid, J., et al., "Real-Time DNA Sequencing from Single Polymerase Molecules", Science, Jan. 2, 2009, vol. 323, pp. 133-138.
List of IBM Patents or Patent Applications Treated As Related dated May 25, 2017 2 pages.

* cited by examiner

INTEGRATED ON CHIP DETECTOR AND ZERO WAVEGUIDE MODULE STRUCTURE FOR USE IN DNA SEQUENCING

BACKGROUND

The present application relates to a semiconductor structure and more particularly to a semiconductor structure that can be used for single molecule real time DNA sequencing applications. The semiconductor structure of the present application includes a photodetector, a zero waveguide module and semiconductor devices integrated on a same semiconductor substrate.

Knowledge of DNA sequences has become indispensable for basic biological research, and in numerous applied fields such as diagnostic, biotechnology, forensic biology, virology and biological systematics. The rapid speed of sequencing attained with modern DNA sequencing technology has been instrumental in the sequencing of complete DNA sequences, or genomes of numerous types and species of life, including the human genome and other complete DNA sequences of many animal, plant, and microbial species.

DNA sequencing is a process of determining the precise order of nucleotide within a DNA molecule. DNA sequencing includes any method that is used to determine the order of the four bases, i.e., adenine, guanine, cytosine and thymine, in a strand of DNA. The advent of rapid DNA sequencing methods has greatly accelerated biological and medical research and discovery.

In some DNA sequencing processes such as, for example, the Sanger method, DNA polymerase has been used as a sequencing engine; DNA polymerase is any of various enzymes that function in the replication and repair of DNA by catalyzing the linking of nucleotides in a specific order, using single-stranded DNA as a template. In such technologies, single DNA molecule detection is required. Some existing single DNA molecule detection techniques are limited to low nanomolar concentrations, in order to reduce background fluorescence or other nucleotides that may be present in solution. At higher concentrations (which are typically required for DNA polymerase implementation), the detection volumes of prior art microscope systems are flooded with hundreds or thousands of labeled molecules. This creates high background noise level which makes it impossible to detect individual fluorophores.

DNA sequencing approaches that circumvent the aforementioned problem by, for example, step-wise addition of base-labeled nucleotides followed by washing, scanning and removal of the label, severely limit the capabilities of the polymerase.

To overcome the above problems, a single molecule real time DNA sequencing technology which enabled the observation of natural DNA synthesis by a DNA polymerase as it occurs was developed by Pacific Biosciences. See, for example, the publication to Eid et al. entitled "Real-Time DNA Sequencing from Single Polymerase Molecules", Science, Vol. 323, 2, January 2009. This single molecule real time DNA sequencing technology includes the use of an apparatus that contains a multiplex zero mode waveguide chip, an optical system, a light source, electronics and a detector. The optical system, detector, electronics and light source employed in such technology are separate components from the multiplex zero mode waveguide chip.

The implementation of separate components in single molecule real time DNA sequencing technology increases the cost of such a process and can reduce the speed and sensitivity of DNA sequencing. As such, there is a need for developing an apparatus for single molecule real time DNA sequencing technology which avoids the drawbacks mentioned above.

SUMMARY

A semiconductor structure for use in single molecule real time DNA sequencing technology is provided in which the optics, electronics and the detector are integrated within a same semiconductor substrate as a plurality of zero waveguide modules. The semiconductor structure of the present application thus reduces the cost of single molecule real time DNA sequencing, while providing higher detection sensitivity and rapid single molecule real time DNA sequencing.

A semiconductor structure for use in single molecule real time DNA sequencing technology is provided. The structure includes a semiconductor substrate including a first region and an adjoining second region. A photodetector is present in the first region and a plurality of semiconductor devices is present in the second region. A contact wire is located on a surface of a dielectric material that surrounds the photodetector and contacts a topmost surface of the photodetector and a portion of one of the semiconductor devices. An interconnect structure is located above the first region and the second region, and a metal layer is located atop the interconnect structure. The metal layer has a zero waveguide module, i.e., opening, located above the first region of the semiconductor substrate. A DNA polymerase can be present at the bottom of the zero waveguide module.

In one aspect of the present application, a semiconductor structure for single molecule real time DNA sequencing is provided. The semiconductor structure of the present application includes a semiconductor substrate comprising a first region and an adjoining second region, wherein at least one photodetector is present in the first region of the semiconductor substrate and located on a portion of a sub-surface of the semiconductor substrate, and wherein a plurality of semiconductor devices is present in the second region of the semiconductor substrate and located on a topmost surface of the semiconductor substrate. The semiconductor structure of the present application further includes a dielectric material surrounding the at least one photodetector and located on exposed portions of the sub-surface of the semiconductor substrate, a contact wire located on a surface of the dielectric material and contacting a topmost surface of the at least one photodetector and a portion of one of the semiconductor devices, an interconnect structure located above the first region and the second region of the semiconductor substrate, the contact wire and the plurality of semiconductor devices, and a metal layer located atop the interconnect structure. The metal layer has a zero waveguide module located above the first region of the semiconductor substrate.

In another aspect of the present application, the present application provides an apparatus for single molecule real time DNA sequencing. The apparatus of the present application includes the semiconductor structure of the present application described above, and DNA polymerase located at a bottom of the zero waveguide module, and a light source located beneath the first region of the semiconductor substrate.

In a further aspect of the present application, a method of forming a semiconductor structure for single molecule real time DNA sequencing is provided. The method includes providing a semiconductor substrate comprising a first region and an adjoining second region, wherein at least one photodetector is formed in the first region of the semiconductor substrate and on a portion of a sub-surface of the semiconductor substrate, and wherein a plurality of semiconductor devices is formed in the second region of the semiconductor substrate and on a topmost surface of the semiconductor substrate. A contact wire contacting a topmost surface of the at least one photodetector and a portion of one of the semiconductor devices is then formed. Next, an interconnect structure is formed above the first region and the second region of the semiconductor substrate, the contact wire and the plurality of semiconductor devices. A metal layer is then provided atop the interconnect structure. The metal layer that is provided has a zero waveguide module located above the first region of the semiconductor substrate.

DETAILED DESCRIPTION

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Figure 1:
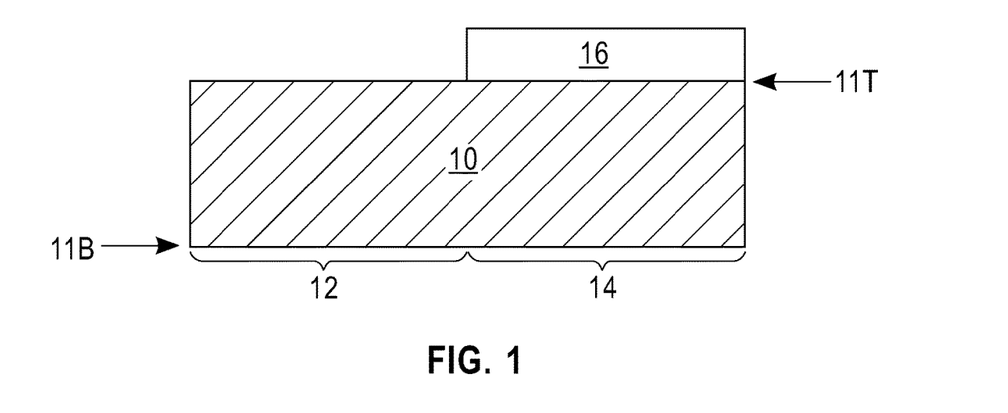
FIG. 1 is a cross sectional view of an exemplary semiconductor structure including a semiconductor substrate having a first region and a second region, wherein a block mask is located over the second region of semiconductor substrate in accordance with an embodiment of the present application.

Referring first to FIG. 1, there is illustrated an exemplary semiconductor structure including a semiconductor substrate 10 having a first region 12 and a second region 14, wherein a block mask 16 is located over the second region 14 of semiconductor substrate 10 in accordance with an embodiment of the present application.

The semiconductor substrate 10 that can be employed in the present application may be a bulk semiconductor substrate. The term "bulk" as used in conjunction with the phrase "semiconductor substrate" denotes that the entire substrate is comprised of at least one semiconductor material. The semiconductor substrate 10 has a first surface, i.e., topmost surface, 11T, and a second surface, i.e., bottommost surface, 11B, which is located opposite the first surface 11T. As shown, the first surface 11T is orientated parallel to the second surface 11B.

In one embodiment of the present application (and as illustrated in the drawings), the semiconductor substrate 10 can be comprised of a single semiconductor material including, but not limited to, Si, Ge, SiGe, SiC, SiGeC, III/V compound semiconductors such as, for example, InAs, GaAs, and InP, and II/VI compound semiconductors. In another embodiment, the semiconductor substrate 10 can be comprised of two or more of the aforementioned semiconductor materials stacked one atop the other. In such an embodiment, semiconductor substrate 10 comprises a multilayered stack of semiconductor materials.

In one embodiment, the semiconductor substrate 10 can be comprised of a single crystalline semiconductor material, such as, for example, single crystalline silicon or single crystalline germanium. In other embodiments, the semiconductor substrate 10 can be comprised of a polycrystalline or an amorphous semiconductor material. When a multilayered stack of semiconductor materials is employed as the semiconductor substrate 10, the multilayered stack may comprise semiconductor materials that are single crystalline, polycrystalline and/or amorphous. The crystal orientation of the semiconductor substrate 10 may be {100}, {110}, or {111}. Other crystallographic orientations besides those specifically mentioned can also be used in the present application.

After selecting the semiconductor substrate 10, block mask 16 can be formed on a portion of the first surface 11T of the semiconductor substrate 10. The portion of the semiconductor substrate 10 not including the block mask 16 can be referred to herein as the first region 12, while the portion of the semiconductor substrate 10 including the block mask 16 can be referred to as the second region 14. In accordance with the present application, first region 12 is a region of the semiconductor substrate 10 in which at least one photodetector will be subsequently formed, while second region 14 is a region of the semiconductor substrate 10 in which semiconductor devices, i.e., transistors, and other circuitry will be subsequently formed.

Block mask 16 can be formed by first providing a contiguous block mask material or materials across the entire first surface 11T of semiconductor substrate 10. The contiguous block mask material that can be used to provide the block mask 16 may include at least one hard mask material such as, for example, silicon dioxide, silicon nitride, or silicon oxynitride. In some embodiments of the present application, the contiguous block mask material that can be used to provide the block mask 16 can be formed by utilizing a deposition process such as, for example, chemical vapor deposition (CVD), plasma enhanced chemical vapor deposition (PECVD), physical vapor deposition (PVD), or evaporation. In other embodiments of the present application, the contiguous block mask material that can be used to provide the block mask 16 can be formed utilizing a thermal growth process such as, for example, oxidation and/or nitridation. In yet other embodiments of the present application, the contiguous block mask material that can be used to provide the block mask 16 can be formed utilizing a combination of a thermal growth technique and a deposition process.

After providing the contiguous block mask material(s), the contiguous block mask material(s) can be patterned utilizing lithography in combination with etching. Lithography includes forming a photoresist material on a topmost exposed surface of the contiguous block mask, exposing a photoresist material to a pattern of irradiation, and then developing the exposed photoresist material utilizing a conventional resist developer. Etching includes an anisotropic wet etch or dry etching process. In some embodiments, and after etching, the photoresist material that is present atop the block mask 16 can be removed utilizing a conventional resist stripping process such as, for example, ashing.

In some embodiments of the present application, the contiguous block mask material that provides the block mask 16 may be entirely composed of a photoresist material. In such an embodiment, the photoresist material can be applied by a deposition process such as, for example, spin-on coating, and lithography alone can be used to pattern the contiguous layer of photoresist material.

Figure 2:
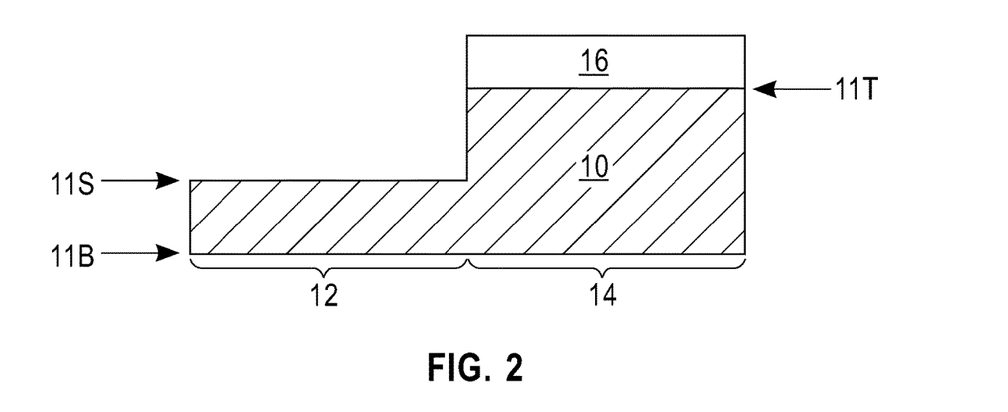
FIG. 2 is a cross sectional view of the exemplary semiconductor structure of FIG. 1 after recessing the first region of the semiconductor substrate that is not protected by the block mask to expose a sub-surface of the semiconductor substrate in the first region in accordance with an embodiment of the present application.

Referring now to FIG. 2, there is illustrated the exemplary semiconductor structure of FIG. 1 after recessing the first region 12 of the semiconductor substrate 10 that is not protected by the block mask 16 to expose a sub-surface 11S of the semiconductor substrate 10 in the first region 12 in accordance with an embodiment of the present application. By "sub-surface" it is meant a surface of the semiconductor substrate that is located parallel to, and between, the first surface 11T and the second surface 11B. In one embodiment of the present application, the sub-surface 11S of the semiconductor substrate 10 in the first region 12 is located from 100 nm to 2000 nm below the first surface 11T. The recessing may be performed utilizing an anisotropic etching process (wet or dry) that is selective in removing semiconductor material relative to the block mask material.

Figure 3:
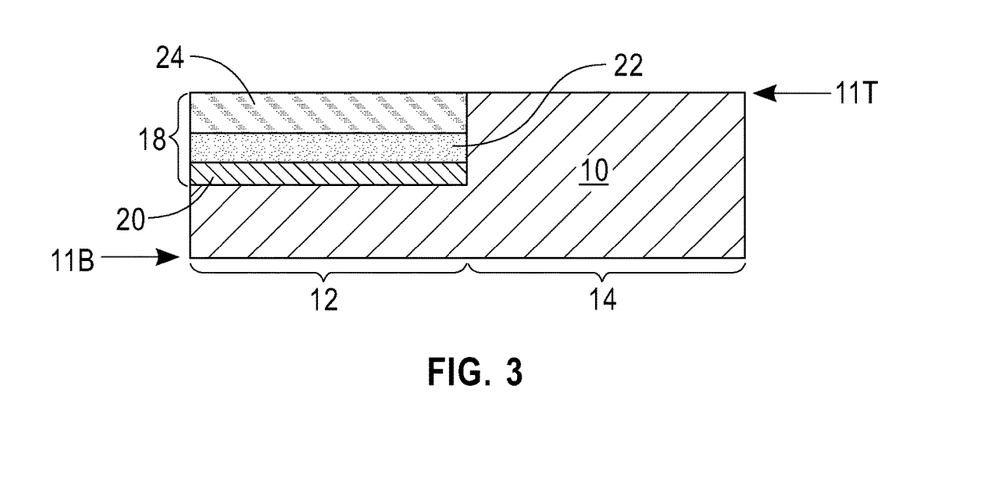
FIG. 3 is a cross sectional view of the exemplary semiconductor structure of FIG. 2 after forming a semiconductor material diode stack on the exposed sub-surface of the semiconductor substrate in accordance with an embodiment of the present application.

Referring now to FIG. 3, there is illustrated the exemplary semiconductor structure of FIG. 2 after forming a semiconductor material diode stack 18 on the exposed sub-surface 11S of the semiconductor substrate 10 in accordance with an embodiment of the present application. The semiconductor material diode stack 18 has a vertical surface that is in direct physical contact with an exposed vertical surface that defines an upper portion of the second region 14 of the semiconductor substrate 10. In some cases, a dielectric material (not shown) can separate the physical contact between the vertical surface of the semiconductor material diode stack 18 and the semiconductor material within an upper portion of the second region 14 of the semiconductor substrate 10. In some embodiments, and as shown, the topmost surface of the semiconductor material diode stack 18 is coplanar with a remaining portion of the first surface 11T of the semiconductor substrate 10. In other embodiments (not shown), the topmost surface of the semiconductor material diode stack 18 is located above or below a remaining portion of the first surface 11T of the semiconductor substrate 10.

In one embodiment of the present application (and as shown), the semiconductor material diode stack 18 includes, from bottom to top, a first semiconductor material 20 of a first conductivity type, a second semiconductor material 22 that is intrinsic, and a third semiconductor material 24 of a second conductivity type that is of an opposite conductivity than the first conductivity. The term "intrinsic" as used throughout the present application denotes a semiconductor material that is non-doped or has a dopant concentration that is less than 1E16 atoms/cm$^3$. In one embodiment, the first conductivity type is n-type, and the second conductivity type is p-type. In such an embodiment, the second semiconductor material 22 can be intrinsic or it can contain an n-type dopant within the range mentioned above. In another embodiment, the first conductivity is p-type, and the second conductivity type is n-type. In such an embodiment, the second semiconductor material 22 can be intrinsic or it can contain a p-type dopant within the range mentioned above.

As used throughout the present application, "p-type" refers the addition of impurities to an intrinsic semiconductor material that creates deficiencies of valence electrons. Examples of p-type dopants, i.e., impurities, in silicon include but are not limited to, boron, aluminum, gallium and indium. In one embodiment, the p-type dopant is present in a concentration ranging from 1E17 atoms/cm$^3$ to 1E21 atoms/cm$^3$. In another embodiment, the p-type dopant is present in a concentration ranging from 1E18 atoms/cm$^3$ to 1E20 atoms/cm$^3$.

As used throughout the present application, "n-type" refers to the addition of impurities that contributes free electrons to an intrinsic semiconductor. Examples of n-type dopants, i.e., impurities, in silicon include but are not limited to, antimony, arsenic and phosphorous. In one embodiment, the n-type dopant is present in a concentration ranging from 1E17 atoms/cm$^3$ to 1E21 atoms/cm$^3$. In another embodiment, the n-type dopant is present in a concentration ranging from 1E18 atoms/cm³ to 1E20.

The first semiconductor material 20, the second semiconductor material 22 and the third semiconductor material 24 that provides the semiconductor material diode stack 18 of the present application include one of the semiconductor materials mentioned above for the semiconductor substrate 10. In some embodiments, at least one of the first semiconductor material 20, the second semiconductor material 22 and the third semiconductor material 24 that provides the semiconductor material diode stack 18 of the present application comprises a same semiconductor material as that of the semiconductor substrate 10. In one example, the semiconductor substrate 10 and the first semiconductor material 20, the second semiconductor material 22 and the third semiconductor material 24 that provides the semiconductor material diode stack 18 of the present application each comprises silicon.

In another embodiment, all three of the first semiconductor material 20, the second semiconductor material 22 and the third semiconductor material 24 that provides the semiconductor material diode stack 18 of the present application comprise different semiconductor materials than the semiconductor substrate 10.

The various semiconductor materials (i.e., 20, 22 and 24) that provide the semiconductor material diode stack 18 can be formed utilizing an epitaxial growth (or deposition) process. The terms "epitaxial growth and/or deposition" and "epitaxially formed and/or grown" mean the growth of a semiconductor material on a deposition surface of a semiconductor material, in which the semiconductor material being grown has the same crystalline characteristics as the semiconductor material of the deposition surface. In an epitaxial deposition process, the chemical reactants provided by the source gases are controlled and the system parameters are set so that the depositing atoms arrive at the deposition surface of a semiconductor material with sufficient energy to move around on the surface and orient themselves to the crystal arrangement of the atoms of the deposition surface. Therefore, an epitaxial semiconductor material that is formed by an epitaxial deposition process has the same crystalline characteristics as the deposition surface on which it is formed. For example, an epitaxial semiconductor material deposited on a {100} crystal surface will take on a {100} orientation. Thus, in the present application, each semiconductor material (i.e., first semiconductor material 20, second semiconductor material 22, and third semiconductor material 24) that provides the semiconductor material diode stack 18 has a same crystal orientation as that of the sub-surface 11S of the semiconductor substrate 10. In some embodiments, epitaxial growth and/or deposition processes are selective to forming on a semiconductor surface, and do not deposit material on dielectric surfaces, such as the block mask 16.

Examples of various epitaxial growth process apparatuses that are suitable for use in forming epitaxial semiconductor material include, e.g., rapid thermal chemical vapor deposition (RTCVD), low-energy plasma deposition (LEPD), ultra-high vacuum chemical vapor deposition (UHVCVD), atmospheric pressure chemical vapor deposition (APCVD) and molecular beam epitaxy (MBE) or metal-organic CVD (MOCVD). The temperature for epitaxial deposition process typically ranges from 250° C. to 900° C. Although higher temperature typically results in faster deposition, the faster deposition may result in crystal defects and film cracking.

A number of different source gases may be used for the deposition of the each semiconductor material (i.e., first semiconductor material 20, second semiconductor material 22, and third semiconductor material 24) that provides the semiconductor material diode stack 18. In some embodiments, the source gas for the deposition include a silicon containing gas source, a germanium containing gas source or a mixture thereof. Carrier gases like hydrogen, nitrogen, helium and argon can be used. Each semiconductor material (i.e., first semiconductor material 20, second semiconductor material 22, and third semiconductor material 24) that provides the semiconductor material diode stack 18 can be epitaxially deposition with or without breaking vacuum between the deposition of the various semiconductor materials.

In one embodiment, the first conductivity type dopant can be introduced into the first semiconductor material 20 by incorporating a first conductivity dopant in-situ during the epitaxial deposition process. In such an embodiment, a gas of the first conductivity type dopant is added to the source gas that provides the first semiconductor material 20. In other embodiments, the first conductivity type dopant can be introduced into the first semiconductor material 20 after first depositing an intrinsic semiconductor material by utilizing one of ion implantation and gas phase doping.

In one embodiment, the second conductivity type dopant can be introduced into the third semiconductor material 24 by incorporating a second conductivity dopant in-situ during the epitaxial deposition process. In such an embodiment, a gas of the second conductivity type dopant is added to the source gas that provides the third semiconductor material 24. In other embodiments, the second conductivity type dopant can be introduced into the third semiconductor material 24 after first depositing an intrinsic semiconductor material by utilizing one of ion implantation and gas phase doping.

The second semiconductor material 22 can be epitaxial deposited in the complete absence of any dopant or a small concentration of the first conductivity dopant can be present during an early stage or the entirety of the epitaxial deposition of the second semiconductor material 22.

In some embodiments, and as shown, the block mask 16 can be removed from the structure at this point of the present application. In such an embodiment, the block mask 16 can be removed utilizing a conventional block mask material removal process. For example, a planarization process, an etching process, a grinding process or a resist stripping process can be used to remove the block mask 16 from the structure. In some embodiments, the block mask 16 remains over the second region 14 of the semiconductor substrate 10 during processing steps that provide the photodetector to the first region 12 of the semiconductor substrate 10.

Figure 4:
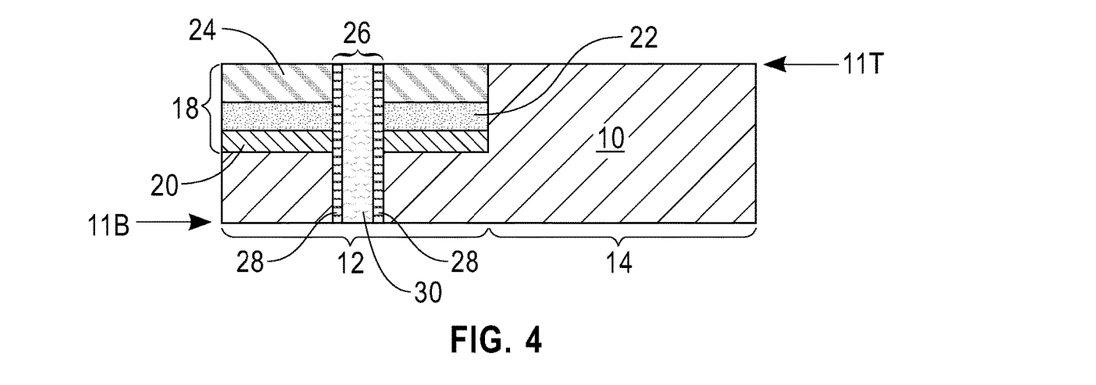
FIG. 4 is a cross sectional view of the exemplary semiconductor structure of FIG. 3 after forming an optical via structure entirely through semiconductor material diode stack and entirely through a remaining portion of the semiconductor substrate that is located directly beneath the semiconductor material diode stack in accordance with an embodiment of the present application.

Referring now to FIG. 4, there is illustrated the exemplary semiconductor structure of FIG. 3 after forming an optical via structure 26 entirely through semiconductor material diode stack 18 and entirely through a remaining portion of the semiconductor substrate 10 that is located within the first region 12 and directly beneath the semiconductor material diode stack 18 in accordance with an embodiment of the present application. Although a single optical via structure 26 is described and illustrated, a plurality of optical via structures can be formed. In some embodiments of the present application, the formation of the optical via structure 26 is omitted and the method continues as described below in providing the structure shown in FIG. 5.

When the optical via structure 26 is present, the optical via structure 26 includes an inner cladding material 30 of a first refractive index that is laterally surrounded by an outer cladding material 28 of a second refractive index that is greater than the first refractive index. Thus, the optical via structure 26 includes an inner cladding material 30 in which light can readily pass through, while the outer cladding material 28 confines the light within the inner cladding material 30. As is shown, a topmost surface of the optical via structure 26 is coplanar with a topmost surface of the semiconductor material diode stack 18 and a remaining portion of the first surface 11T of the semiconductor substrate. As is further shown, a bottommost surface of the optical via structure 26 is coplanar with second surface 11B of the semiconductor substrate 10. As is also shown outer, upper sidewall surfaces of the outer cladding material 28 are in direct physical contact with a sidewall surface of the semiconductor material diode stack 18, while outer, lower sidewall surfaces of the outer cladding material 28 are in direct physical contact with the semiconductor substrate 10.

The outer cladding material 28 may comprise a dielectric material that has a dielectric constant, as measured in a vacuum, of about 4.0 or less. In one example, the outer cladding material 28 may comprise silicon dioxide. In some embodiments of the present application, the inner cladding material 30 may comprise amorphous silicon or polysilicon. The term "amorphous" denotes that the material lacks any well defined crystal structure. In another embodiment of the present application, the inner cladding material 30 comprises silicon nitride. In such an embodiment, the silicon nitride inner cladding material 30 may have a silicon concentration of from 50 atomic percent to 80 atomic percent. Other silicon concentrations for a silicon nitride inner cladding material are also possible.

The optical via structure 26 can be formed by first providing a through via opening into semiconductor material diode stack 18 and into a remaining portion of the semiconductor substrate 10 that is located within the first region 12 and directly beneath the semiconductor material diode stack 18. The through via opening may be formed by lithography and anisotropic etching. After providing the through via opening, the outer cladding material 28 is deposited on the vertical sidewalls of the through via opening, and then the inner cladding material 30 is deposited within a remaining volume of the through via opening.

Figure 5:
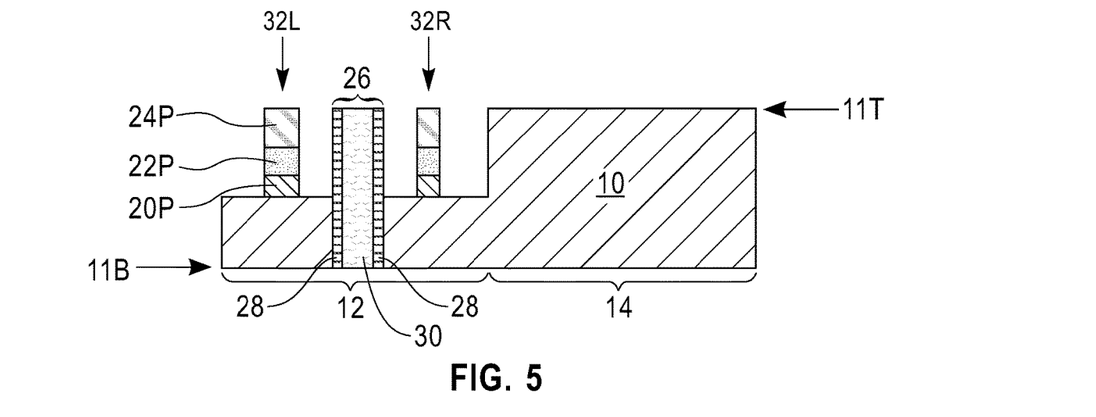
FIG. 5 is a cross sectional view of the exemplary semiconductor structure of FIG. 4 after patterning the semiconductor material diode stack to provide semiconductor nanowire photodetectors located on either side of the optical via structure in accordance with an embodiment of the present application.

Referring now to FIG. 5, there is illustrated the exemplary semiconductor structure of FIG. 4 after patterning the semiconductor material diode stack 18 to provide semiconductor nanowire photodetectors 32L, 32R located on either side of the optical via structure 24 in accordance with an embodiment of the present application. The semiconductor nanowire photodetectors 32L, 32R can be formed by lithography and etching.

Each semiconductor nanowire photodectector 32L, 32R comprises a remaining portion of the first semiconductor material 20 of the first conductivity type (hereinafter first semiconductor material portion 20P), a remaining portion of the second semiconductor material 22 that is intrinsic (hereinafter second semiconductor material portion 22P), and a remaining portion of the third semiconductor material 24 of the second conductivity type that is opposite that first conductivity (hereinafter third semiconductor material portion 24P).

As shown, the semiconductor nanowire photodetector 32L has a first diameter (i.e., width), while the semiconductor nanowire photodetector 32R has a second diameter (i.e., width) that is different from the first diameter. The first and second diameters are tailored to correspond with a wavelength of fluorophore used in the present application. In one embodiment of the present application, the first diameter of semiconductor nanowire photodetector 32L can be from 30 nm to 50 nm, while the second diameter of the semiconductor nanowire photodetector can be from 50 nm to 100 nm. In another embodiment of the present application, the first diameter of semiconductor nanowire photodetector 32L can be from 30 nm to 40 nm, while the second diameter of the semiconductor nanowire photodetector can be from 60 nm to 80 nm.

The present application is not limited to forming a pair of semiconductor nanowire photodetectors. Instead, any number of semiconductor nanowire photodetectors including a single photodetector can be formed, as desired. The diameters of the plurality of semiconductor nanowire photodetectors that are formed can be tailored to correspond with a wavelength of fluorophore used for adenine, guanine, cytosine and thymine.

As shown, semiconductor nanowire photodetectors 32L, 32R have vertical sidewall surface that are perpendicular to the sub-surface portion 11S of the semiconductor substrate 10. As is also shown, the semiconductor nanowire photodetectors 32L, 32R have topmost surfaces that are coplanar with each other. As is further shown, the semiconductor nanowire photodetectors 32L, 32R are not in direct contact with any portion of the optical via structure 26.

It should be noted that the present application is not limited to forming semiconductor nanowire photodetectors. Instead, the semiconductor nanowire photodetectors can be replaced with other types of photodetectors such, as for example, a metal Schottky photodetector. The other types of photodetectors can be processed on sub-surface 11S utilizing techniques that are well known to those skilled in the art.

Figure 6:
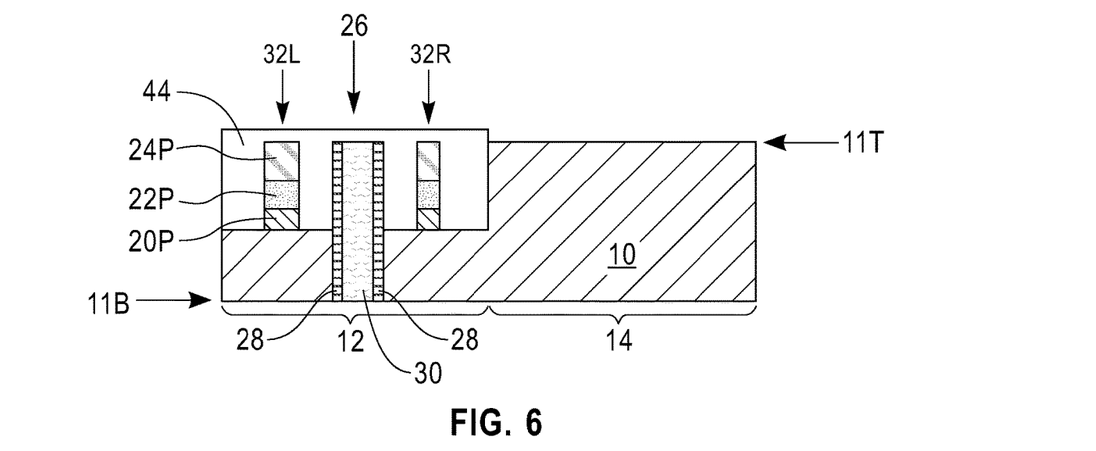
FIG. 6 is a cross sectional view of the exemplary semiconductor structure of FIG. 5 after formation of a dielectric material in accordance with an embodiment of the present application.

Referring now to FIG. 6, there is illustrated the exemplary semiconductor structure of FIG. 5 after formation of a dielectric material 44 in accordance with an embodiment of the present application. Dielectric material 44 is light transparent. As is shown, the dielectric material 44 surrounds the exposed surfaces (vertical and topmost) of each of the semiconductor nanowire photodetectors 32L, 32R, and, if present, the exposed surfaces (vertical and topmost) of the optical via structure 26. A portion of the dielectric material 44 is also located directly on a sidewall surface of the remaining semiconductor substrate 10 within the second region 14.

In some embodiments, the dielectric material 44 may be composed of, for example, silicon dioxide, undoped silicate glass (USG), fluorosilicate glass (FSG), borophosphosilicate glass (BPSG), a spin-on low-k dielectric layer, a chemical vapor deposition (CVD) low-k dielectric layer or any combination thereof. The term "low-k" as used throughout the present application denotes a dielectric material that has a dielectric constant of less than silicon dioxide. In another embodiment, a self-planarizing material such as a spin-on glass (SOG) or a spin-on low-k dielectric material such as SiLK™ can be used as the dielectric material 44. The use of a self-planarizing dielectric material as dielectric material 44 may avoid the need to perform a subsequent planarizing step.

In one embodiment, the dielectric material 44 can be formed utilizing a deposition process including, for example, chemical vapor deposition (CVD), plasma enhanced chemical vapor deposition (PECVD), low pressure CVD, rapid thermal CVD, evaporation or spin-on coating. A block mask (not shown) may be present over the second region 14 of the semiconductor substrate 10 during the formation of dielectric material 44. In some embodiments, particularly when non-self-planarizing dielectric materials are used as dielectric material 44, a planarization process or an etch back process follows the deposition of the dielectric material 44. The thickness of the dielectric material 44 that can be employed in the present application may vary depending on the type of dielectric material employed as well as the method that was employed in forming the same. In one embodiment, the dielectric material 44 has a thickness from 80 nm to 500 nm. Other thicknesses that are greater or lesser than the range provided above can also be used for the dielectric material 44.

Figure 7:
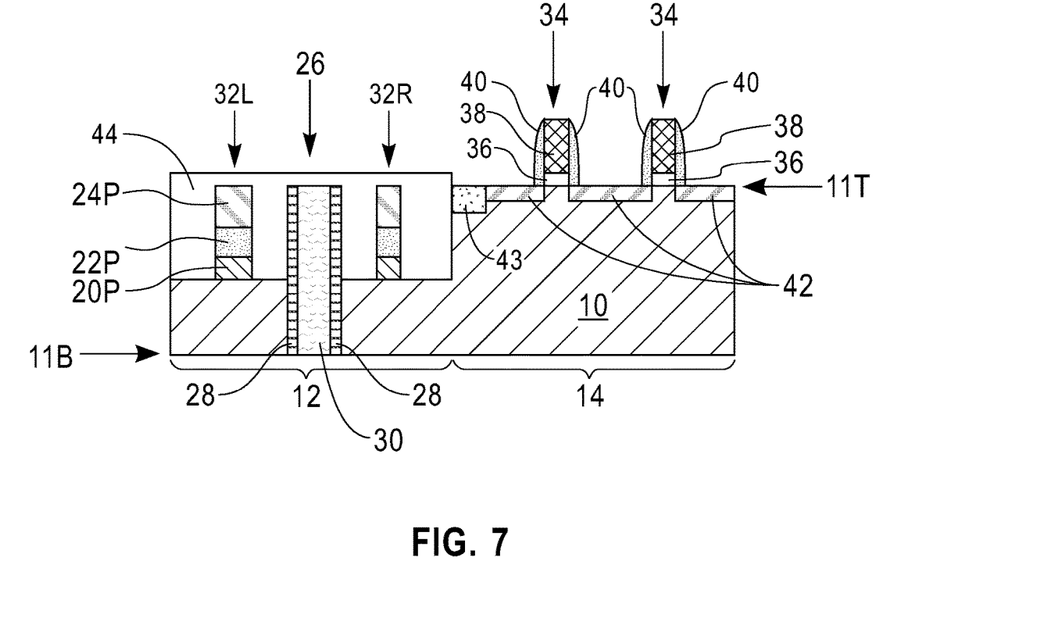
FIG. 7 is a cross sectional view of the exemplary semiconductor structure of FIG. 6 after forming a plurality of transistors within the second region of the semiconductor substrate in accordance with an embodiment of the present application.

Referring now to FIG. 7, there is illustrated the exemplary semiconductor structure of FIG. 6 after forming a plurality of transistors 34 within the second region 14 of the semiconductor substrate 10 in accordance with an embodiment of the present application. In some embodiments of the present application, the plurality of transistors 34 can be all of the same conductivity type (i.e., n-type or p-type). In another embodiment of the present application, a first set of transistors of the plurality of transistors can be p-type transistors, while a second set of transistors of the plurality of transistors can be n-type transistors. Although not shown, a plurality of transistors can be processed in another portion of the semiconductor substrate 10 which lies adjacent and to the left of the first region 12 shown in the drawings.

The plurality of transistors 34 include a gate structure that contains, a gate dielectric portion 36, and an overlying gate conductor portion 38. A dielectric spacer 40 can be present on sidewall surfaces of each gate structure (36, 38). Each transistor 34 also includes a source region and a drain region (collectively referred to herein as source/drain regions 42) that is located within the semiconductor substrate 10 and at a footprint of each gate structure (36, 38).

The plurality of transistors 34 can be formed utilizing a gate first or a gate last process as is well known to those skilled in the art. In a gate first process, each gate structure is formed first followed by the source/drain regions. In a gate last process, each gate structure is formed after source/drain regions are formed. In such a process, a sacrificial gate structure is first provided and then source/drain regions are formed. Next, the sacrificial gate structure may be replaced with a functional gate structure. Each gate structure (36, 38) may be referred to as a functional gate structure. The term "functional gate structure" is used throughout the present application as a permanent gate structure used to control output current (i.e., flow of carriers in the channel) of a semiconducting device through electrical or magnetic fields. The functional gate structure, i.e., transistors 34 form electronic components of the semiconductor structure of the present application.

The gate dielectric material that provides each gate dielectric material portion 36 can be an oxide, nitride, and/or oxynitride. In one example, the gate dielectric material that provides each gate dielectric material portion 36 can be a high-k material having a dielectric constant greater than silicon dioxide. Exemplary high-k dielectrics include, but are not limited to, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, SiON, $SiN_x$, a silicate thereof, and an alloy thereof. Each value of x is independently from 0.5 to 3 and each value of y is independently from 0 to 2. In some embodiments, a multilayered gate dielectric structure comprising different gate dielectric materials, e.g., silicon dioxide, and a high-k gate dielectric can be formed.

The gate dielectric material used in providing each gate dielectric material portion 36 can be formed by any deposition technique including, for example, chemical vapor deposition (CVD), plasma enhanced chemical vapor deposition (PECVD), physical vapor deposition (PVD), sputtering, or atomic layer deposition. In some embodiments, a thermal process including, for example, thermal oxidation and/or thermal nitridation may be used in forming each gate dielectric material portion 36. When a different gate dielectric material is used for the gate dielectric material portions, block mask technology can be used. In one embodiment of the present application, the gate dielectric material used in providing each gate dielectric material portion 36 can have a thickness in a range from 1 nm to 10 nm. Other thicknesses that are lesser than or greater than the aforementioned thickness range can also be employed for the gate dielectric material.

Each gate conductor portion 38 comprises a gate conductor material. The gate conductor material used in providing each gate conductor portion 38 can include any conductive material including, for example, doped polysilicon, an elemental metal (e.g., tungsten, titanium, tantalum, aluminum, nickel, ruthenium, palladium and platinum), an alloy of at least two elemental metals, an elemental metal nitride (e.g., tungsten nitride, aluminum nitride, and titanium nitride), an elemental metal silicide (e.g., tungsten silicide, nickel silicide, and titanium silicide) or multilayered combinations thereof. The gate conductor material used in providing each gate conductor portion 38 can be formed utilizing a deposition process including, for example, chemical vapor deposition (CVD), plasma enhanced chemical vapor deposition (PECVD), physical vapor deposition (PVD), sputtering, atomic layer deposition (ALD) or other like deposition processes. When a metal silicide is formed, a conventional silicidation process is employed. When a different gate conductor material is used for the gate conductor portions, block mask technology can be used. In one embodiment, the gate conductor material used in providing each gate conductor portion 38 has a thickness from 1 nm to 100 nm. Other thicknesses that are lesser than or greater than the aforementioned thickness range can also be employed for the gate conductor material used in providing each gate conductor portion 36.

Dielectric spacer 40 can be formed prior to or after gate structure formation. Each dielectric spacer 40 comprises a dielectric spacer material such as silicon dioxide and/or, silicon nitride. The dielectric spacer 40 can be formed be deposition of a dielectric spacer material and thereafter etching of the dielectric spacer material.

Source/drain regions 42 can be formed by introducing a dopant into the exposed portions of semiconductor substrate 10 and at the footprint of either the sacrificial gate structure or at the footprint of the permanent gate structures. The dopant can be n-type or p-type, as defined above, and can be introduced via an ion implantation process. The concentration of dopants used in providing the source/drain regions 42 can range from 5E18 atoms/cm$^3$ to 1.5E21 atoms/cm$^3$.

In some embodiments of the present application, the semiconductor substrate 10 in the second device region 14 may be processed to include at least one trench isolation structure. Notably, trench isolation structure 43 is formed in the second region 14 of the semiconductor substrate 10 that is nearest to the first region 12 to prevent the short of contact wire 46R (to be subsequently formed) to the semiconductor substrate 10. The trench isolation structure 43 can be formed utilizing any conventional trench isolation process. For example, trench isolation structure 43 can be formed by forming a trench within the second region 14 of the semiconductor substrate utilizing lithography and etching. The trench can then be filled with a trench dielectric material such as, for example, silicon dioxide. A planarization process may follow the filling of the trench with the trench dielectric material.

Although the present application describes and illustrates the formation of the semiconductor nanowire photodetectors 32L, 34R and dielectric material 44 prior to forming the plurality of transistors 34, the order of formation can be reversed such that the plurality of transistors 34 are formed prior to processing the first region 12 of the semiconductor substrate 10, e.g., prior to exposing the sub-surface 11S and/or forming the semiconductor nanowire photodetectors 32L, 32R and dielectric material 44. It is further noted that during the processing of the plurality of transistors 34, the first region 12 of the semiconductor substrate 10, with or without exposing the sub-surface 11S, and/or the formation of semiconductor nanowire photodetectors 32L, 32R and dielectric material 44, can be protected by a block mask.

It is noted that the present application is not limited to forming a plurality of transistors 34 within the second region 14 of the semiconductor substrate 10. Other semiconductor devices can be formed in lieu of, or in conjunction with, the plurality of transistors 34.

Figure 8:
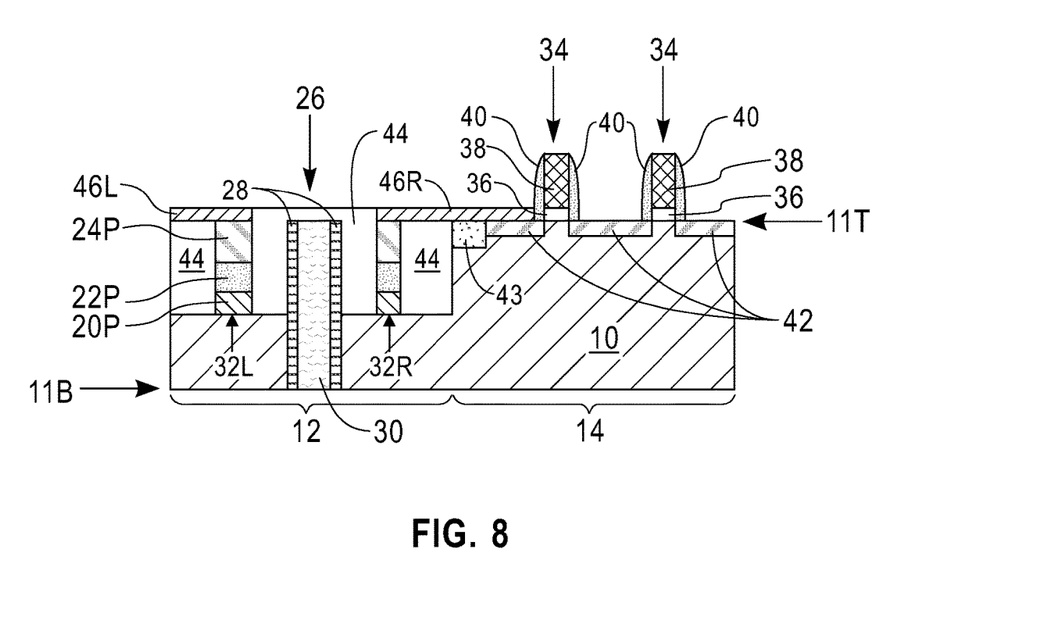
FIG. 8 is a cross sectional view of the exemplary semiconductor structure of FIG. 7 after formation of contact wires in accordance with an embodiment of the present application.

Referring now to FIG. 8, there is illustrated the exemplary semiconductor structure of FIG. 7 after formation of contact wires 46L, 46R in accordance with an embodiment of the present application. As shown, at least a portion of a bottommost surface of contact wire 46L is in direct physical contact with a topmost surface of semiconductor nanowire photodetector 32L, while at least a portion of a bottommost surface of contact wire 46R is in direct physical contact with semiconductor nanowire photodetector 32R. Contact wires 46L, 46R extend across a recessed surface of the dielectric material 44. In the illustrated embodiment, contact wire 46R also extends onto trench isolation region 43 in the second region 14 and makes contact with a portion of at least one of the transistors of the plurality of transistors 34; contact wire 46L would also extend onto a trench isolation region and make contact with one of the transistors within another portion of the semiconductor substrate 10 that is located to the left of the first region 12 shown in the drawings. As is also shown, the topmost surface of contact wires 46L, 46R are coplanar a topmost surface of a portion of the dielectric material 44 that remains over the optical via structure 26.

The contact wires 46L, 46R comprise an elemental metal, or an alloy containing at least two elemental metals. Examples of materials that can provide the contact wires 46L, 46R include copper (Co), tungsten (W), aluminum (Al) and alloys thereof such as, for example, a copper-aluminum alloy. The contact wires 46L, 46R can be formed by first recessing portions of dielectric material 44 that are located directly atop the semiconductor nanowire photodetectors 32L, 32R so as to exposed a topmost surface of each of the semiconductor nanowire photodetectors 32L, 32R. Next, a layer of an elemental metal or a layer of an alloy thereof is formed by a deposition process such as, for example, CVD, PECVD, sputtering or plating. These elemental metal-containing layers are then patterned by lithography and etching providing contact wires 46L, 46R. The thickness of the contact wires 46L, 46R can be in a range from 20 nm to 200 nm. Other thicknesses that are lesser than or greater than the aforementioned thickness range can also be employed as the thickness of the contact wires 46L, 46R.

Figure 9:
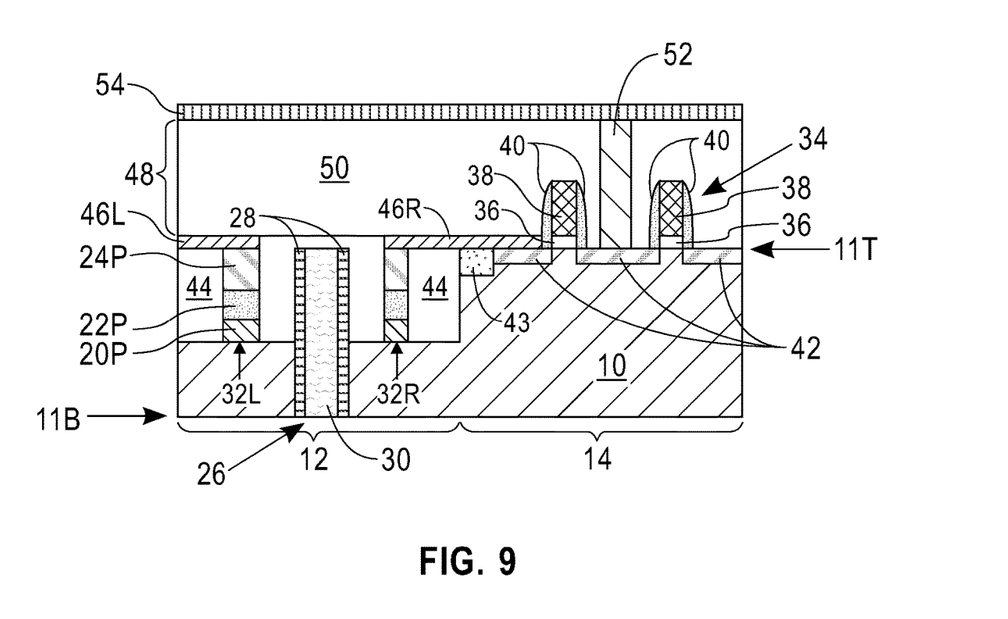
FIG. 9 is a cross sectional view of the exemplary semiconductor structure of FIG. 8 after forming an interconnect structure in accordance with an embodiment of the present application.

Referring now to FIG. 9, there is illustrated the exemplary semiconductor structure of FIG. 8 after forming an interconnect structure 48 in accordance with an embodiment of the present application. The interconnect structure 48 includes an interconnect dielectric material 50 that includes at least one metal structure 52 embedded within the interconnect dielectric material 50. As is shown, the interconnect structure 48 extends over the first region 12 and the second region 14 of the semiconductor substrate 10.

The interconnect structure 48 can be formed utilizing any known process including, for example, a single damascene or a dual damascene process. In some embodiments, the metal structure 52 is formed first and then the interconnect dielectric material 50 is formed.

The interconnect dielectric material 50 that can be employed in the present application may include any interlevel or intralevel dielectric including inorganic and organic dielectrics. Interconnect dielectric material 50 is light transparent. The interconnect dielectric material 50 typically has a dielectric constant of about 4.0 or less. Some examples of suitable dielectrics that can be used as the interconnect dielectric material 50 include, but are not limited to, silicon dioxide, silsesquioxanes, C doped oxides (i.e., organosilicates) that include atoms of Si, C, 0 and H, thermosetting polyarylene ethers or multilayers thereof. The term "polyarylene" is used in this application to denote aryl moieties or inertly substituted aryl moieties which are linked together by bonds, fused rings, or inert linking groups such as, for example, oxygen, sulfur, sulfone, sulfoxide, carbonyl and the like. The interconnect dielectric material 50 may be porous or non-porous. Porous dielectrics are advantages since such dielectrics have a lower dielectric constant than an equivalent non-porous dielectric material.

The interconnect dielectric material 50 can be formed utilizing a deposition process such as, for example, CVD, PECVD, spin-on coating, evaporation or chemical solution deposition. The thickness of the interconnect dielectric material 50 can be in a range from 50 nm to 1000 nm. Other thicknesses that are lesser than or greater than the aforementioned thickness range can also be employed as the thickness of the interconnect dielectric material 50.

The metal structure 52 embedded within the interconnect dielectric material 50 may include one of the materials mentioned above for the contact wires 46L, 46R. In one embodiment, the metal structure 52 comprises a same material as the contact wires 46L, 46R. In another embodiment, the metal structure 52 comprises a different material as the contact wires 46L, 46R. The metal structure 52 may be a conductive via, a conductive line or combinations of conductive vias and lines. For simplicity, metal structure 52 is shown as being a conductive via.

In some embodiments and as shown in FIG. 9, a topmost metal structure embedded within the interconnect dielectric material 50 has a topmost surface that is coplanar with a topmost surface of the interconnect dielectric material 50.

Still referring to FIG. 9, a dielectric capping layer 54 can be formed over the entirety of the interconnect structure 48. Dielectric capping layer 54 is light transparent. In some embodiments, the dielectric capping layer 54 can be omitted. The dielectric capping layer 54 comprises any dielectric capping material including, for example, one of the dielectric materials mentioned above for the interconnect dielectric material 50. Other examples of dielectric capping materials that can be employed to provide the dielectric capping layer 54 include silicon nitride, $Si_4NH_3$, or a nitrogen and hydrogen doped silicon carbide, i.e., SiC(N,H). Any multilayered combination of the aforementioned dielectrics may be employed as the dielectric capping layer 54. The dielectric capping layer 54 can be formed utilizing one of the deposition process as mentioned above for forming the interconnect dielectric material 50. The thickness of the dielectric capping layer 54 is typically from 30 nm to 60 nm.

Although thicknesses that are lesser than or greater than the aforementioned thickness range may also be used in the present application as the thickness of the dielectric capping layer 54.

Figure 10:
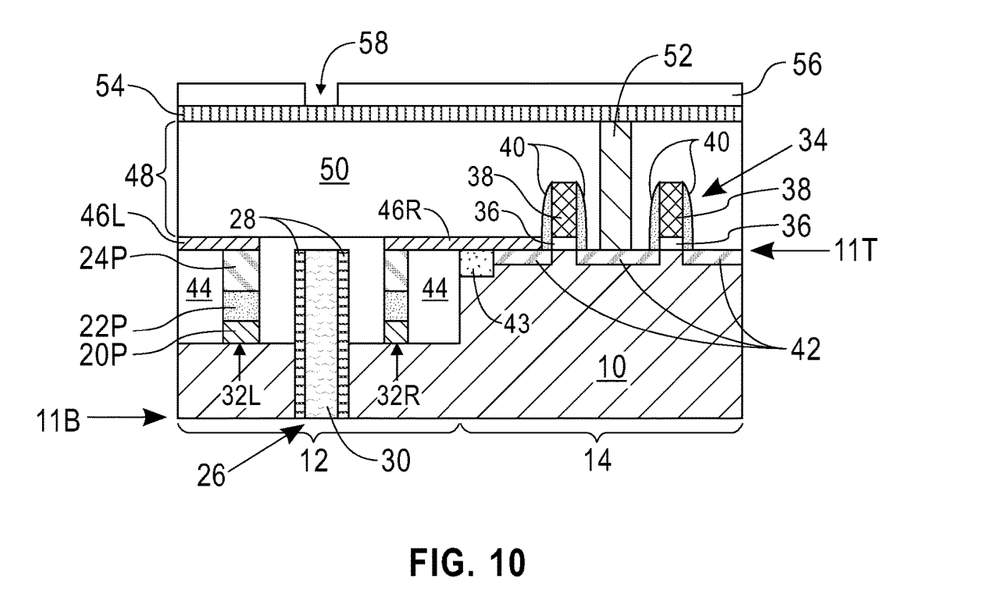
FIG. 10 is a cross sectional view of the exemplary semiconductor structure of FIG. 9 after forming a metal layer containing an opening atop the interconnect structure in accordance with an embodiment of the present application.

Referring now to FIG. 10, there is illustrated the exemplary semiconductor structure of FIG. 9 after forming a metal layer 56 containing an opening 58 atop the interconnect structure 48 in accordance with an embodiment of the present application. The opening 58 that is formed within the metal layer 56 provides a zero waveguide module of the present application. Although a single zero waveguide module is described and illustrated, a plurality of zero waveguide modules can be formed as desired.

The metal layer 56 can be formed by first providing a contiguous metal-containing layer atop the interconnect structure 48; in the illustrated embodiment, the contiguous metal-containing layer is formed directly on the entirety of the dielectric capping layer 54. The contiguous metal-containing layer that provides metal layer 56 may include an elemental metal including, for example, Cu, Al, W, Ni, or Pt. In one embodiment of the present application, the contiguous metal-containing layer that provides metal layer 56 may comprise a same elemental metal as the contact wires 46L, 46R. In another embodiment of the present application, the contiguous metal-containing layer that provides metal layer 56 may comprise a different elemental metal as the contact wires 46L, 46R. In one embodiment, Al is employed as the contiguous metal-containing layer that provides metal layer 56. The contiguous metal-containing layer that provides metal layer 56 can be formed utilizing a deposition process including, for example, CVD, PECVD, sputtering, atomic layer deposition (ALD), PVD or plating. The contiguous metal-containing layer that provides metal layer 56 can have a thickness from 20 nm to 200 nm. Other thicknesses that are lesser than or greater than the aforementioned thickness range can also be employed as the thickness of the contiguous metal-containing layer that provides metal layer 56.

Opening 58 is then formed in the contiguous metal-containing layer. In the illustrated embodiment, the opening 58 is formed above the optical via structure 26 and between the semiconductor nanowire photodetectors 32L, 32R. The opening 58 can be formed by perforating the contiguous metal-containing layer that provides metal layer 56 by utilizing techniques well known to those skilled in the art. For example, the perforation of the contiguous metal-containing layer that provides metal layer 56 may be performed by wet etch using acid solution or using reactive ion etching. The opening 58 has a width from 5 nm to 50 nm.

At this point of the present application, the metal layer 56 that includes opening 58 can be treating with a chemical agent that prohibits DNA polymerase from sticking to the surface of the metal layer 58. In one example, the chemical agent that can be used to prohibit DNA polymerase from sticking to the metal layer 56 includes polyvinylphosphonic acid (PVPA).

Figure 11:
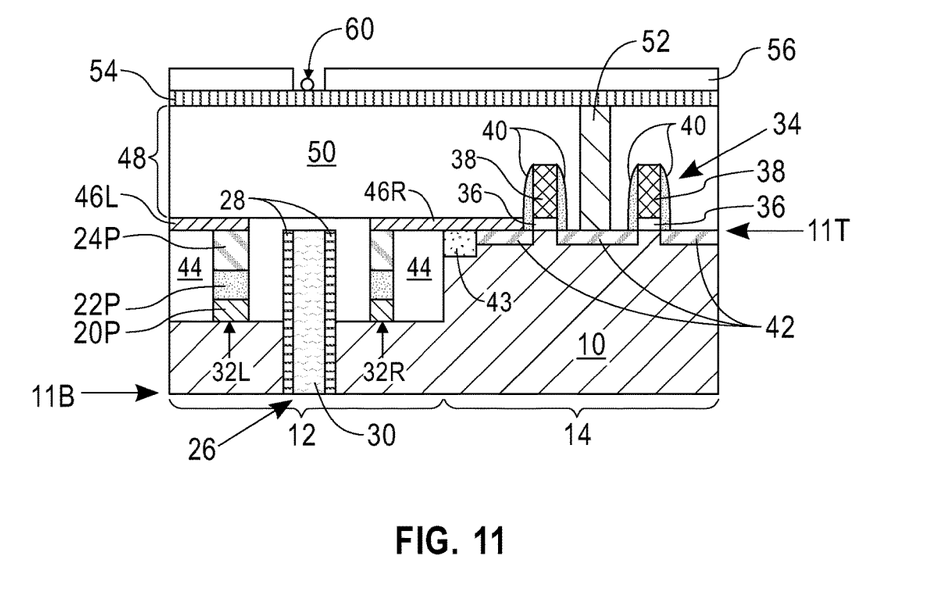
FIG. 11 is a cross sectional view of the exemplary semiconductor structure of FIG. 10 after depositing a DNA polymerase within the opening in accordance with an embodiment of the present application.

Referring now to FIG. 11, there is illustrated the exemplary semiconductor structure of FIG. 10 after depositing a single DNA polymerase 60 within the opening 58 in accordance with an embodiment of the present application. By "DNA polymerase" it is meant any enzyme that can create DNA molecules assembling nucleotides that are the basic building blocks of DNA. These enzymes are essential to DNA replication and usually work in pairs to create two identical DNA strands from a single original DNA molecule. During this process, DNA polymerase "reads" the existing DNA strands to create two new strands that match the existing ones. When creating DNA, DNA polymerase can add free nucleotides only to the 3' end of the newly forming strand. This results in elongation of the newly forming strand in a 5'-3' direction. Examples of such DNA polymerase 60 that can be employed in the present application include Prokaryotic or Eukaryotic DNA polymerases. In one embodiment, Prokaryotic Family A polymerases can be used.

The DNA polymerase 60 can be formed within the opening 58 utilizing techniques well known to those skilled in the art. In one example, the DNA polymerase 60 can be formed utilizing an immobilization process.

Figure 12:
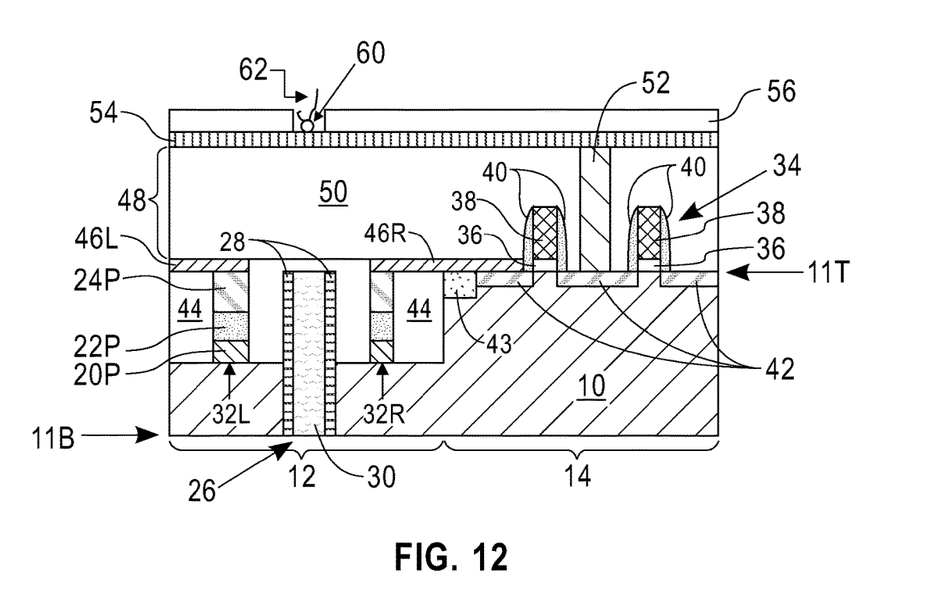
FIG. 12 is a cross sectional view of the exemplary semiconductor structure of FIG. 11 after attaching a DNA template to a surface of the DNA polymerase in accordance with an embodiment of the present application.

Referring now to FIG. 12, there is illustrated the exemplary semiconductor structure of FIG. 11 after attaching a DNA template 62 to a surface of the DNA polymerase 60 in accordance with an embodiment of the present application. By "DNA template" it is meant any single strand of DNA on which a new strand of DNA are made following the complementary base pairing rules. A primer can also be attached to the DNA to enable the starting process of the DNA replication.

The DNA template 62 is provided in a solution that also contains various nucleotides with a fluorophore; the fluorophore is typically attached to the various nucleotides. By "fluorophore" it is meant a fluorescent compound that can re-emit light upon light excitation. Fluorophores typically contain several combined aromatic groups, or plane or cyclic molecules with several π bonds. Fluorophore molecules could be generally classified into four categories: proteins and peptides, small organic compounds, synthetic oligomers and polymers, and multi-component systems. Some examples of fluorophore that can be used in the present application include, xanthene derivative, cyanine derivatives, squaraine derivatives, napthalene derivatives, coumarin derivatives, oxadiazole derivatives, anthracene derivatives, pyrene derivatives, oxazine derivatives, acridine derivatives, arylmethine derivatives or tetrapyrrole derivatives.

By "nucleotides" it is meant organic molecules that serve as the monomers, or subunits, of nucleic acids, like DNA and RNA. The building blocks of nucleic acids, nucleotides are composed of a nitrogenous base (i.e., one of adenine (A), guanine (G), thymine (T) and cytosine (C)), a five-carbon sugar (ribose or deoxyribose), and at least one phosphate group.

In accordance with the present application, the solution containing the DNA template 62 with attached primer, and nucleotides with attached fluorophore is added to the structure shown in FIG. 12 utilizing techniques that are well known to those skilled in the art. For example, the solution containing the DNA template 62 and attached primer, and nucleotides with attached fluorophore can be added by drop wise addition from a dropper or pipette. After addition of the above mentioned solution, the DNA template 62 becomes attached to the DNA polymerase 60. The nucleotides then attach to the DNA template 62 according to sequence and when light is present, light emission is generated at the bottom of the opening 58. This is shown, for example, in FIG. 13.

Figure 13:
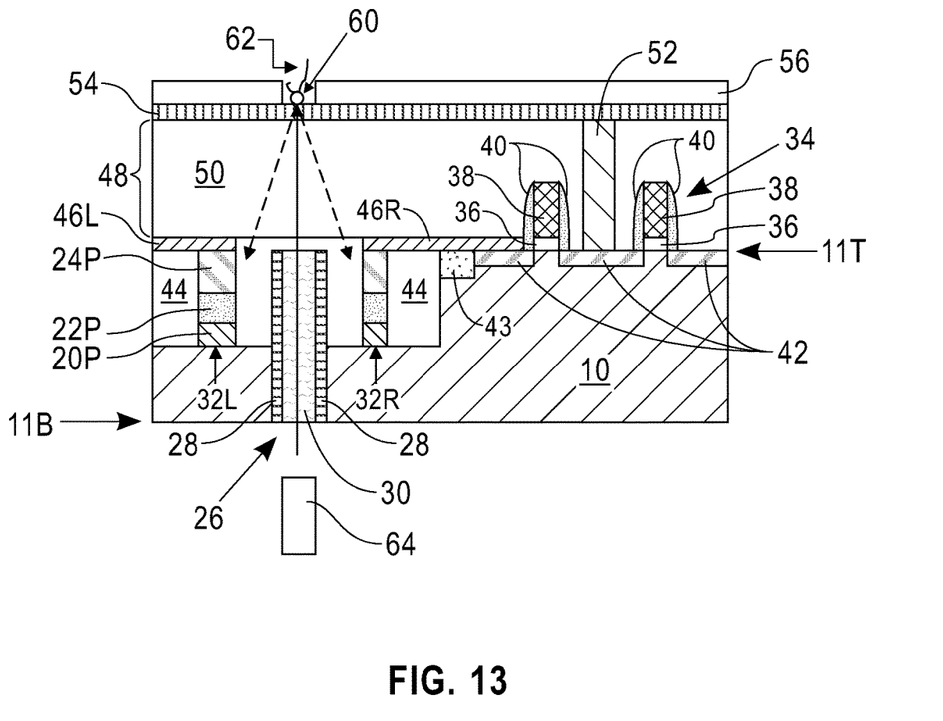
FIG. 13 is cross sectional view of the exemplary semiconductor structure of FIG. 12 after positioning a light source beneath the first region of the semiconductor substrate in accordance with an embodiment of the present application.

Referring now to FIG. 13, there is illustrated the exemplary semiconductor structure of FIG. 12 after positioning a light source 64 beneath the first region 12 of the semiconductor substrate 10 in accordance with an embodiment of the present application. The light source 64 may comprise any light source including, for example, a laser. The solid arrow represents light emitted from the light source 64 which passing though a bottommost surface 11B of the semiconductor substrate 10. If optical via structure 24 is present, the light can be collected and passed though the inner cladding material 30. The collected light that passes through the topmost surface of the optical via structure and continues through the overlying interconnect dielectric material 50 and through the dielectric capping layer 54. As mentioned above, and during the DNA sequencing process, the nucleotides attach to the DNA template 62 according to sequence and when light is present, light emission is generated at the bottom of the opening 58. Due to the width of the opening 58, this light emission is reflected back through the dielectric capping layer 54 and the interconnect dielectric material 50 and gets detected by the semiconductor nanowire photodetectors 32L, 32R. The light emitted from the above sequencing is represented by the dotted lines with arrows. The detector signal can then be transmitted from the semiconductor nanowire photodetectors 32L, 32R through the contact wires 46L, 46R and then processed by the transistors 34 and outputted to a microprocessor which can in communication with the metal structures 52 of the interconnect structure 48.

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A method of forming a semiconductor structure, said method comprising:
    providing a semiconductor substrate comprising a first region and an adjoining second region, wherein at least one photodetector is formed in said first region of said semiconductor substrate and on a portion of a sub-surface of said semiconductor substrate, and wherein a plurality of semiconductor devices is formed in said second region of said semiconductor substrate and on a topmost surface of said semiconductor substrate;
    forming a contact wire contacting a topmost surface of said at least one photodetector and a portion of one of said semiconductor devices;
    forming an interconnect structure above said first region and said second region of said semiconductor substrate, said contact wire and said plurality of semiconductor devices;
    providing a metal layer above a topmost surface of said interconnect structure, wherein said metal layer has an opening that provides a zero waveguide module located above said first region of said semiconductor substrate; and
    forming a dielectric material laterally surrounding said at least one photodetector and directly on an exposed sub-surface of said semiconductor substrate, wherein said dielectric material is formed prior to forming said plurality of semiconductor devices.

2. The method of claim 1, wherein said at least one photodetector is a semiconductor nanowire photodetector.

3. The method of claim 2, wherein said semiconductor nanowire photodetector comprises, from bottom to top, a first semiconductor material portion of a first conductivity type, a second semiconductor material portion that is intrinsic, and a third semiconductor material portion of a second conductivity type, wherein said second conductivity type is opposite from said first conductivity type.

4. The method of claim 1, further comprising forming an optical via structure in said first region of said semiconductor substrate and located adjacent, but not in contact, with said at least one photodetector.

5. The method of claim 4, wherein said optical via structure comprises an inner cladding material laterally surrounded by an outer cladding material, wherein said inner cladding material has a refractive index that is less than a refractive index of said outer cladding material.

6. The method of claim 4, wherein a topmost surface of said optical via structure is coplanar with a topmost surface of said at least one photodetector.

7. The method of claim 1, further comprising forming a DNA polymerase at a bottom of said opening that provides said zero waveguide module.

8. The method of claim 7, further comprising attaching a DNA template to a surface of said polymerase and initiating a DNA sequencing process.

9. The method of claim 1, further comprising providing a light source beneath said first region of said semiconductor substrate.

10. The method of claim 9, wherein said light source is a laser.

11. The method of claim 1, wherein said at least one photodetector is formed prior to forming said semiconductor devices.

12. The method of claim 11, wherein said at least one photodetector is formed by:
    recessing a physically exposed portion of said semiconductor substrate in said first region to expose a sub-surface of said semiconductor substrate;
    forming a semiconductor material diode stack on said exposed sub-surface of said semiconductor substrate in said first region; and
    patterning said semiconductor material diode stack to provide said at least one photodetector.

13. The method of claim 12, wherein said forming said semiconductor material stack comprises:
    forming a first semiconductor material of a first conductivity type;
    forming a second semiconductor material, said second semiconductor material is an intrinsic semiconductor material; and
    forming a third semiconductor material of a second conductivity type that is opposite the first conductivity type.

14. The method of claim 12, wherein said patterning comprising lithography and etching.

15. The method of claim 14, wherein prior to said patterning, an optical via structure is formed, wherein said optical via structure is present in said first region and extends completely through a remaining portion of said semiconductor substrate in said first region.

16. The method of claim 15, wherein said optical via structure is formed by:
    providing a through via opening into said semiconductor material diode stack and into said remaining portion of said semiconductor substrate;
    forming an outer cladding material along the vertical sidewalls of said though via opening; and
    forming an inner cladding material in a remaining volume of said through via opening wherein said inner cladding material has a refractive index that is less than a refractive index of said outer cladding material.

17. The method of claim 1, wherein said at least one photodetector is a metal Schottky Photodetector.

18. The method of claim 1, wherein said dielectric material is light transparent.

\* \* \* \* \*